US011596477B2

(12) United States Patent
Brannan

(10) Patent No.: US 11,596,477 B2
(45) Date of Patent: Mar. 7, 2023

(54) SYSTEMS AND METHODS FOR GENERATING ENERGY DELIVERY HEAT MAPS

(71) Applicant: Covidien LP, Mansfield, MA (US)

(72) Inventor: Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 768 days.

(21) Appl. No.: 16/159,111

(22) Filed: Oct. 12, 2018

(65) Prior Publication Data
US 2019/0151025 A1 May 23, 2019

Related U.S. Application Data

(60) Provisional application No. 62/588,469, filed on Nov. 20, 2017.

(51) Int. Cl.
*A61B 34/10* (2016.01)
*A61B 18/22* (2006.01)
(Continued)

(52) U.S. Cl.
CPC .............. *A61B 34/10* (2016.02); *A61B 18/12* (2013.01); *A61B 18/1815* (2013.01); *A61B 18/22* (2013.01); *A61B 34/25* (2016.02); *A61B 90/36* (2016.02); *A61B 90/37* (2016.02); *A61B 18/02* (2013.01); *A61B 2018/0066* (2013.01);
(Continued)

(58) Field of Classification Search
CPC ..... A61B 18/18; A61B 18/1815; A61B 18/22; A61B 18/1206; A61B 18/1233; A61B 2018/1823; A61B 2018/00577; A61B 2018/00636; A61B 2018/0066; A61B 2018/00779; A61B 2018/00702; A61B 2018/00988; A61B 34/25; A61B 34/10; A61B 2034/107; A61B 2034/254;
(Continued)

(56) References Cited

U.S. PATENT DOCUMENTS 6,322,558 B1 11/2001 Taylor et al.
8,369,930 B2 2/2013 Jenkins et al.
(Continued)

FOREIGN PATENT DOCUMENTS

WO 2011123669 A1 10/2011
WO 2017197114 A1 11/2017

OTHER PUBLICATIONS

Extended European Search Report issued in corresponding Appl. No. EP 18206798.3 dated Apr. 15, 2019 (9 pages).
(Continued)

*Primary Examiner* — Thomas A Giuliani
(74) *Attorney, Agent, or Firm* — Carter, DeLuca & Farrell LLP

(57) ABSTRACT

A system for recording or recalling ablation information includes a workstation, and control circuitry. The workstation may include a display, a user input device, and a memory. The workstation may be configured to be in electrical communication with an ablation device. The control circuitry may be in electrical communication with the ablation device and the memory. The control circuitry may be configured to receive input associated with an ablation procedure performed by the ablation device, and associate the input with an anatomical structure of the patient.

15 Claims, 6 Drawing Sheets

(51) Int. Cl.
*A61B 18/18* (2006.01)
*A61B 90/00* (2016.01)
*A61B 34/00* (2016.01)
*A61B 18/12* (2006.01)
*A61B 18/00* (2006.01)
*A61B 18/16* (2006.01)
*A61B 18/02* (2006.01)

(52) U.S. Cl.
CPC .............. *A61B 2018/00404* (2013.01); *A61B 2018/00494* (2013.01); *A61B 2018/00529* (2013.01); *A61B 2018/00535* (2013.01); *A61B 2018/00541* (2013.01); *A61B 2018/00577* (2013.01); *A61B 2018/00589* (2013.01); *A61B 2018/00601* (2013.01); *A61B 2018/00636* (2013.01); *A61B 2018/00779* (2013.01); *A61B 2018/00791* (2013.01); *A61B 2018/00827* (2013.01); *A61B 2018/00875* (2013.01); *A61B 2018/00886* (2013.01); *A61B 2018/00988* (2013.01); *A61B 2018/167* (2013.01); *A61B 2034/107* (2016.02); *A61B 2034/254* (2016.02); *A61B 2034/256* (2016.02); *A61B 2090/365* (2016.02); *A61B 2090/3762* (2016.02)

(58) Field of Classification Search
CPC ... A61B 2034/256; A61B 90/36; A61B 90/37; A61B 2090/365; A61B 2090/3762
USPC ............ 606/33, 34, 38, 42; 607/98, 99, 101, 607/113, 115, 116, 154, 156
See application file for complete search history.

(56) References Cited

U.S. PATENT DOCUMENTS

| | | | |
|---|---|---|---|
| 8,517,923 | B2 | 8/2013 | Belson et al. |
| 8,702,690 | B2 | 4/2014 | Paul et al. |
| 9,113,888 | B2 | 8/2015 | Orszulak et al. |
| 9,247,992 | B2 | 2/2016 | Ladtkow et al. |
| 9,259,290 | B2 | 2/2016 | Jenkins et al. |
| 9,459,770 | B2 | 10/2016 | Baker |
| 9,639,666 | B2 | 5/2017 | Baker |
| 9,925,009 | B2 | 3/2018 | Baker |
| 2013/0165854 | A1 | 6/2013 | Sandhu et al. |
| 2013/0282005 | A1 | 10/2013 | Koch et al. |
| 2014/0081262 | A1* | 3/2014 | Koblish ............. A61B 18/1492 606/41 |
| 2015/0018698 | A1* | 1/2015 | Safran .................... G16Z 99/00 600/508 |
| 2016/0000302 | A1 | 1/2016 | Brown et al. |
| 2016/0317229 | A1 | 11/2016 | Girotto et al. |
| 2017/0325891 | A1* | 11/2017 | Harlev .................. A61B 34/20 |
| 2018/0116751 | A1 | 5/2018 | Schwartz et al. |

OTHER PUBLICATIONS

Chinese Office Action issued in corresponding application, 201811379529.3, dated Aug. 12, 2021, together with English language translation (14 pages).

* cited by examiner

SYSTEMS AND METHODS FOR GENERATING ENERGY DELIVERY HEAT MAPS

CROSS REFERENCE TO RELATED APPLICATION

The present application claims priority to U.S. Provisional Patent Application No. 62/588,469 filed on Nov. 20, 2017, the entire contents of which are incorporated herein by reference.

FIELD

The present disclosure is directed to systems and methods for tracking surgical procedure information. Specifically, the present disclosure is directed to systems and methods for storing and recalling ablation histories over time. More particularly, the present disclosure is directed to systems and methods for generating energy delivery heat maps.

BACKGROUND

Surgical procedures incorporating ablation techniques are employed as therapeutic treatments for eliminating diseased tissue located within patients. For example, as abnormal or diseased tissue is identified with scans or by visual inspection, surgeons may choose to perform one or more procedures to deliver energy to the diseased tissue and, in certain cases, the surrounding tissue in an effort to eliminate the diseased tissue. One example of such a surgical procedure is an ablation procedure. Ablation procedures may include the application of cryogenic energy (cryo-energy), electrosurgical energy (i.e., microwave energy or radio frequency (RF) energy), or other forms of energy for ablating tissue.

The tissue which is targeted by the surgeon during the ablation procedure, or the "target tissue," may encompass part or all of the diseased tissue. Depending on the goals of the surgeon treating the diseased tissue, energy may be applied to the target tissue during a single surgical procedure, or across a span of multiple procedures. For example, where the diseased portion of the target tissue is significant or encompasses an area which is greater than can be treated in a single surgical procedure, the target tissue may be treated across multiple surgical procedures to support patient recovery.

Prior to the ablation, surgeons may review one or more files indexing the locations of the diseased tissue to determine which areas of tissue are to be targeted for treatment. Patient histories may be recorded manually by surgeons or their assistants during each surgical procedure on anatomical structure diagrams. Additionally, or alternatively, medical images including optical or scanned images of the anatomical structures may be marked or otherwise annotated by surgeons before, during, or after surgical procedures. These images, which collectively form the ablation history of the patient, may be stored and referenced over time as the patient is treated.

SUMMARY

Accordingly, it is desirable to provide systems and methods of maintaining and selectively delivering persistent information regarding the history of ablation of one or more anatomical structures of a patient.

According to an example embodiment herein, a system for recording or recalling ablation information includes a workstation and control circuitry. The workstation includes a display, a user input device, and a memory. The workstation may be configured to be in electrical communication with an ablation device. The control circuitry may be in electrical communication with the ablation device and the memory. The control circuitry is configured to receive input associated with an ablation procedure performed by the ablation device, and associate the input with an anatomical structure of a patient.

According to aspects, the input is received from either the ablation device or the user input device. The system may include a representation of a default anatomical structure stored in the memory of the workstation. The representation of the default anatomical structure may include a plurality of anchor points and a plurality of splines extending therebetween to define extents of the default anatomical structure.

In aspects, the control circuitry may be configured to associate a default anatomical structure with the anatomical structure of the patient, receive input to adjust a position of at least one anchor point relative to the default anatomical structure to form a representative anatomical structure of the patient, and store the representative anatomical structure of the patient in the memory of the workstation. The representative anatomical structure of the patient may approximate features of the anatomical structure of the patient.

According to aspects, the control circuitry is configured to form an ablation region along the representative anatomical structure in response to receiving input at the workstation. The ablation region may include a plurality of anchor points and a plurality of splines associated with the plurality of anchor points. Forming the ablation regions may further include associating ablation procedure information with the ablation region. The ablation procedure information may include information associated with a state of target tissue or a state of the ablation device.

In aspects, the control circuitry is configured to transmit signals to cause the display to display an illustration of the representative anatomical structure.

According to aspects, forming an ablation region along the representative anatomical structure may include forming a first ablation region and a second ablation region along the anatomical structure. A plurality of ablation regions may be formed along the representative anatomical structure. The first ablation region may at least partially intersect the second ablation region. The control circuitry may be configured to transmit signals to cause the display to display an illustration of the representative anatomical structure, the illustration including the first ablation region and the second ablation region. The first ablation region may be illustrated with a first color, and the second ablation region may be illustrated with a second color.

In aspects, the system may include an ablation system including the ablation device.

According to an example embodiment herein, a method of recalling ablation information during a surgical procedure is described. The method includes selecting a default anatomical feature stored in a memory of a workstation, receiving input from an input device of the workstation, modifying one or more anchor points associated with the anatomical feature based on the received input, and storing the modified anatomical feature in the memory of the workstation.

In aspects, the method further includes receiving sensor data from an ablation system, displaying the sensor data on a display device coupled to the workstation, receiving input from the input device after displaying the sensor data, and associating the sensor data with the stored anatomical feature based on the received input. The sensor data may include at least one of a tissue temperature, a tissue thermal mass, a tissue dielectric constant, a tissue stiffness, and a tissue impedance.

According to aspects, the method may include displaying, on the display device, a plurality of anchor points and a plurality of corresponding splines between the plurality of anchor points to form an ablation region. The sensor data may be associated with the ablation region.

In aspects, the method may include displaying on the display device the anatomical feature, the ablation region, and the sensor data associated with the ablation region. The method may further include receiving orientation input from the input device, and displaying on the display device the anatomical feature in an updated orientation based on the received orientation input.

BRIEF DESCRIPTION OF THE DRAWINGS

The accompanying drawings, which are incorporated in and constitute a part of the specification, illustrate embodiments of the disclosure and, together with the general description of the disclosure given above, and the detailed description of the embodiment(s) given below, serve to explain the principles of the disclosure.

DETAILED DESCRIPTION

Figure 1:
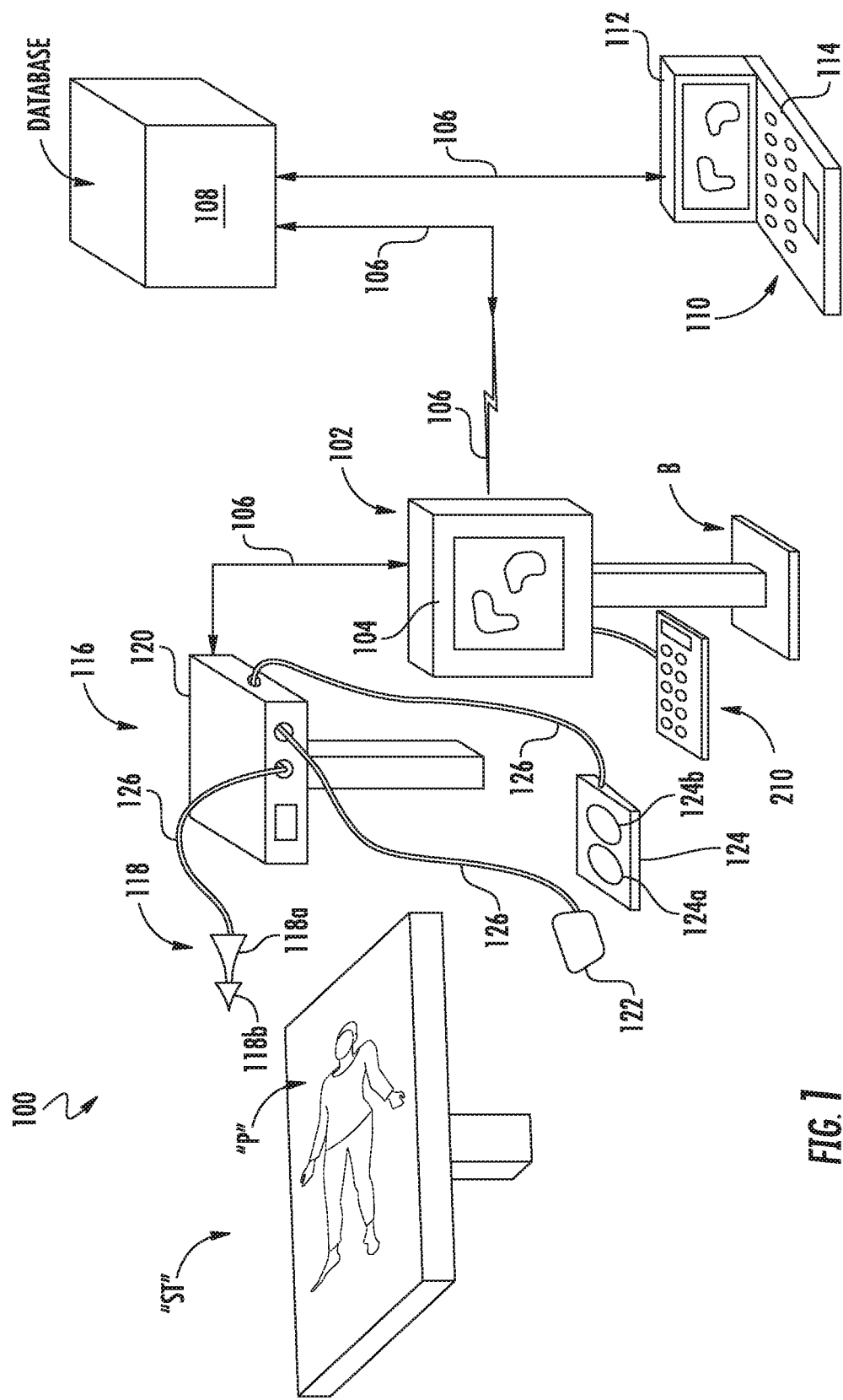
FIG. 1 is a perspective view of an ablation heat map recordation system, according to an embodiment of the present disclosure.

Embodiments of the present disclosure are described in detail with reference to the drawings, in which like reference numerals may designate identical or corresponding elements in each of the several views.

The present disclosure is directed to an ablation recording systems and methods which record user-input related to ablation procedures, the user-input recorded to track and display an ablation history of a patient. The ablation recording systems thus enable surgeons to visually inspect the ablation history of the patient, and determine whether subsequent treatments would be desirable during the course of treatment of the patient. Additionally, the visualized ablation history enable surgeons to determine which areas of tissue that include diseased tissue have not received ablation treatment, or if the ablation treatment provided to the patient have yielded desirable results. These systems may also allow for the recordation of anatomic abnormalities due to either natural occurrence (i.e., the patient is born with a deformed organ) or due to surgical therapies such as resection or removal of tissue from the patient.

Throughout this description, the term "clinician" refers to individuals who provide or assist in providing therapeutic treatments to patients such as, without limitation, doctors, surgeons, nurses, and other such support staff. The term "proximal" refers to the portion of the device, component, or anatomical feature that is closer to a clinician, and the term "distal" refers to the portion of the device or component thereof that is farther from the clinician. The phrases "in an embodiment," "in embodiments," or "in other embodiments," may each refer to one or more of the same or different embodiments in accordance with the present disclosure. Further, while reference may be made to elements in the singular, such distinction is intended only to simplify such description and is not intended to limit the subject matter of the present disclosure.

With reference to FIG. 1, an ablation recording system is illustrated and designated generally 100. Ablation recording system 100 includes a workstation 102, a surgical table "ST" with a patient "P" disposed thereon, a recordation database or database 108, and a remote workstation 110. Table "ST" may be any suitable table capable of maintaining patient "P" thereon during an ablation procedure. Workstation 102, remote workstation 110, and database 108 are electrically coupled (or in a wired configuration) via wires 106. It is contemplated that electrical communication between workstation 102, remote workstation 110, and database 108 may be achieved via wireless configurations such as radio frequency, optical, WiFi®, Bluetooth®, or other such suitable wireless configurations. For purposes of clarity, wireless and/or wired electrical communication such as those described hereinabove will be referred to herein as "electrical communication". In embodiments, workstation 102, remote workstation 110, and database 108, or any subset thereof, may be combined into a single workstation and be interconnected therein.

Workstation 102, remote workstation 110, and database 108 may be, for example, a laptop computer, a desktop computer, a tablet computer, a thin-client in electrical communication with a remote database, or other similar devices. Workstation 102, remote workstation 110, and database 108 may include some or all of the components illustrated in FIG. 2 to enable reception of user-input, execution of instructions, and/or output or display of information related to the recordation of information associated with one or more ablation procedures. Additionally, workstation 102, remote workstation 110, and database 108 may be configured to receive user-inputs including, without limitation, audio input, video input, keyboard/mouse input, scanned images, tactile input, and the like.

With continued reference to FIG. 1, ablation of target tissue of patient "P" is performed with an ablation system 116 including an electrosurgical instrument or ablation device 118, an electrosurgical generator 120, and electrosurgical accessories such as a return electrode pad 122 and ablation pedals 124. The components of the ablation system 116 couple via wired connections 126 to the electrosurgical generator 120. The electrosurgical generator 120 may include control circuitry (not explicitly shown) which enables electrical communication between the components of the ablation system 116. Additionally, the control circuitry of the electrosurgical generator 120 may be coupled to workstation 102 to enable electrical communication therebetween. While, for clarity, reference will now be made to ablation procedures including radio frequency (RF) energy, one skilled in the art will readily appreciate that the present disclosure is not confined to the application of RF energy to target tissue and, rather, that procedures implementing any known ablation procedure (e.g., cryoablation, microwave ablation, etc.) may be monitored and recorded in accordance with principles as described by the present disclosure.

For a detailed description of ablation systems, reference may be made to U.S. Pat. Nos. 9,247,992 and 9,113,888, the entire contents of each of which are incorporated herein by reference.

Figure 2:
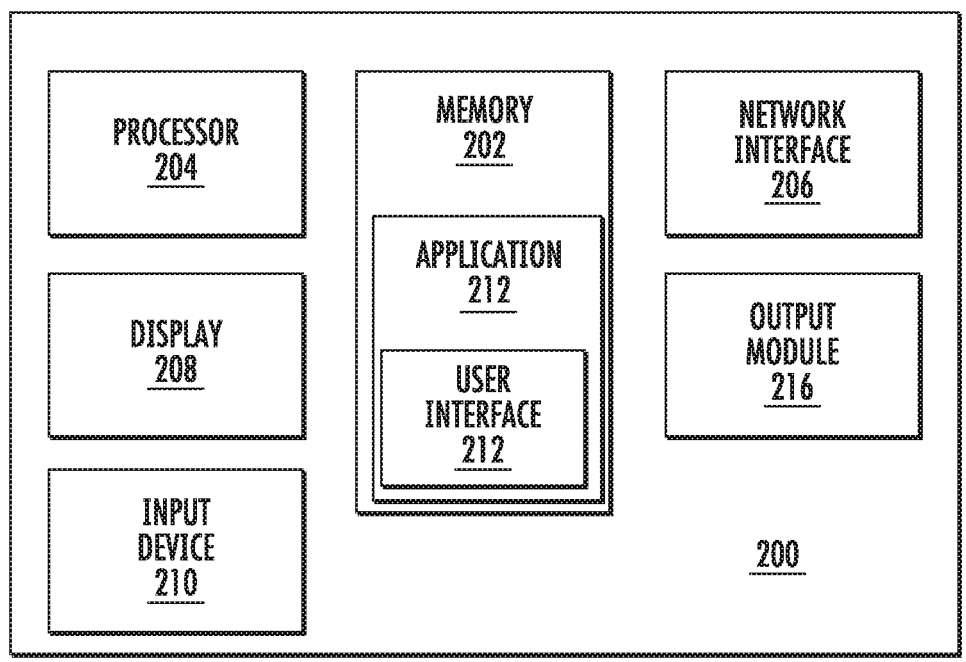
FIG. 2 is a schematic diagram of components associated with a workstation configured for use with the system of FIG. 1.

Referring to FIG. 2, illustrated is a system diagram of system components which may be included in or associated with workstation 102, remote workstation 110, or database 108, the system diagram illustrating a system designated generally 200. System 200 may include a memory 202, a processor 204, network interfaces 206, a display 208, one or more input devices 210, and an output module 216.

Display 208 may be any suitable display device capable of projecting images thereon, such as a liquid crystal display (LCD), a light emitting diode (LED) display, and the like. Display 208 is in electrical communication with, and configured to receive signals from, processor 204. As processor 204 transmits signals to display 208, the signals are converted to images which are output by display 208 to clinicians. Display 208 may further include integrated speakers (not explicitly shown) embedded in a housing of display 208, the integrated speakers configured to output audible signals based on the received signals from processor 204. Additionally, display 208 may be configured to receive touch or tactile input, and subsequently transmit sensor signals indicative of the tactile input to processor 204.

Memory 202 may include transitory-type media, i.e., RAM, and/or non-transitory computer-readable media, i.e., flash media or disk media, for storing data. Data stored in memory 202 may include instructions executable by processor 204. Processor 204, which is in electrical communication with memory 202, is configured to execute instructions or computer programs which are stored in memory 202 to augment or otherwise manipulate data stored in memory 202. In this regard, the processor 204 includes any suitable logic control circuit adapted to perform calculations and/or operate according to a set of instructions. Instructions executed by processor 204 may control operation of workstation 102, remote workstation 110, and database 108, including initiating transmission of data or communication therebetween. Additionally, memory 202 may include instructions which enable reception of input data from input devices 210 or display 208. It is contemplated that memory 202 may be stored remotely and accessed, such remote storage and retrieval of data referred to generally in the art as cloud computing.

Figure 3:
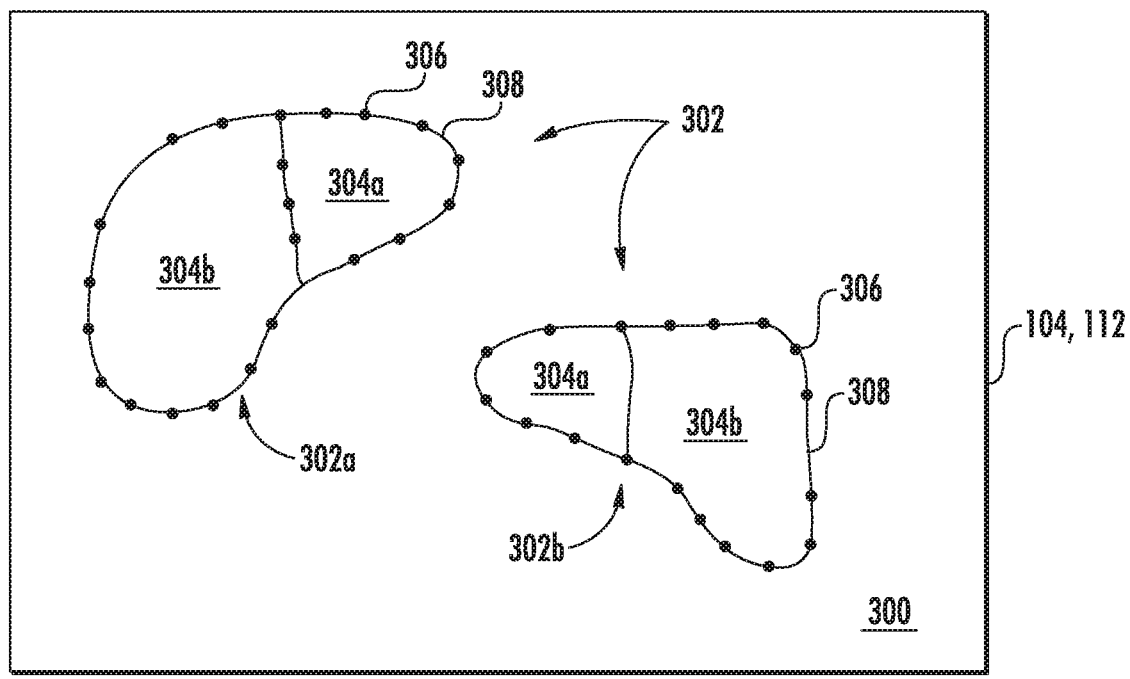
FIG. 3 is an illustration of a user interface, including a view of an anatomical structure, according to an embodiment of the present disclosure.

FIG. 3 illustrates an interface which includes an image to be shown on display 104, remote display 112, or a display (not shown) associated with database 108, the interface designated generally 300. Interface 300 includes a first plan view or view 302a and a second plan view or view 302b, i.e., two two-dimensional (2D) representations, of a representation of a liver 302 of patient "P". The representation of the liver of patient "P", liver 302, may be a predefined anatomical representation of a generic liver stored in memory 202. Alternatively, liver 302 may be a representation of the liver of patient "P" captured during imaging of the liver of patient "P". Such representations may be associated with three-dimensional models of the liver generated based on a series of computed tomography (CT) scans, or other such suitable scanning systems. For a detailed discussion of three-dimensional model generation, reference may be made to commonly-owned U.S. patent Ser. Nos. 13/838,805, 13/838,997, and 13/839,224, the entire contents of each of which are incorporated herein by reference. While interface 300 may include an individual view, or a plurality of views of one or more anatomical structures of patient "P", for purposes of simplicity description of the principles of the present disclosure will be made with regard to views 302a, 302b. Likewise, interface 300 may display three-dimensional (3D) representations of liver 302. It is further contemplated that liver 302 may be viewed with 3D display devices such as Samsung Gear VR goggles, or displays which project 2D representations for reception via polarized films or polarized glasses.

With continued reference to FIG. 3, a first liver region 304a and a second liver region 304b are displayed within interface 300. First and second liver regions 304a, 304b are defined by a lines or splines 308 which extend between anchor points 306. More particularly, splines 308 define the extents or boundaries of liver 302 of patient "P". Splines 308 may be modified or removed by repositioning or deleting respective anchor points 306 disposed along interface 300. As such, splines 308 may be adjusted to reflect anomalies or abnormalities of a particular patient with respect to default anatomical features when liver 302 is associated with patient "P" prior to performing one or more surgical procedures on patient "P". Further, as surgical procedures are performed on patient "P", clinicians may adjust splines 308 so as to accurately reflect the results of the procedure performed on patient "P" such as, for example, indicating that a portion of liver 302 was resected during the surgical procedure. For example, when a default representation of an anatomical structure is selected among one or more anatomical structures stored in memory 202 (FIG. 2) as representing liver 302 of patient "P", liver 302 may not include deformations or landmarks located on or associated with liver 302 of patient "P". The clinician may modify the default representation of the selected anatomical structure by repositioning anchor points 306 and by extension associated splines 308 in order to increase the accuracy of liver 302 via input device 210.

Over time, as clinicians ablate or otherwise modify portions of the liver of patient "P" during surgical procedures, the clinicians may add anchor points 306 to liver 302, and connect the anchor points 306 with splines 308 to represent ablations performed to liver 302. Specifically, clinicians may input commands to move or delete anchor points 306, and by extension splines 308, via input device 210 of workstation 102 to modify the stored representation of the liver of patient "P", liver 302. Similarly, when portions of the liver of patient "P" are resected, or otherwise removed, clinicians may modify liver 302 stored in memory 202 by moving or deleting anchor points 306 and/or splines 308.

Modifications made by clinicians of liver 302 may be stored in a history included in memory 202, including information associated with the procedures performed by clinicians on patient "P". For example, when clinicians perform a series of surgeries to treat one or more target tissue areas associated with the liver of patient "P", the clinicians may amend the representation of the liver of patient "P", i.e., liver 302, to reflect the areas of target tissue which were ablated during each procedure. (see FIG. 6) Such amendments may include identifying portions of target tissue which received energy during the one or more procedures. Clinicians may additionally include contextual information, including notes and images taken during or after each surgery, to provide context for later display when reviewing the history of patient "P". As a result of the persistent storage of liver 302 in memory 202, including modifications of liver 302 over time (FIGS. 1-4), an ablation heat map (see FIG. 6) may be generated indicating target tissue which has been ablated during treatments administered to patient "P".

Additionally, clinicians may modify liver 302 stored in memory 202 in preparation for one or more surgical procedures. For example, clinicians may visually inspect liver 302 stored in memory 202 in view of the ablation history associated with liver 302 and determine a desired sequence of subsequent ablation procedures. Remote clinicians may also review liver 302 stored in memory 202 from remote workstation 110 to assist treating clinicians in diagnosing and planning ablation procedures. By virtue of the persistence of liver 302 in memory 202, which may be stored or mirrored in workstation 102, database 108, or remote workstation 110, along with the associated treatment history of liver 302, clinicians may view the liver of patient "P", including scans or other imaging of the liver of patient "P" in light of planned ablation or resection procedures. In embodiments, imaging of the liver of patient "P" (not explicitly shown) may be superimposed on the representation of liver 302 in memory 202.

Figure 4A:
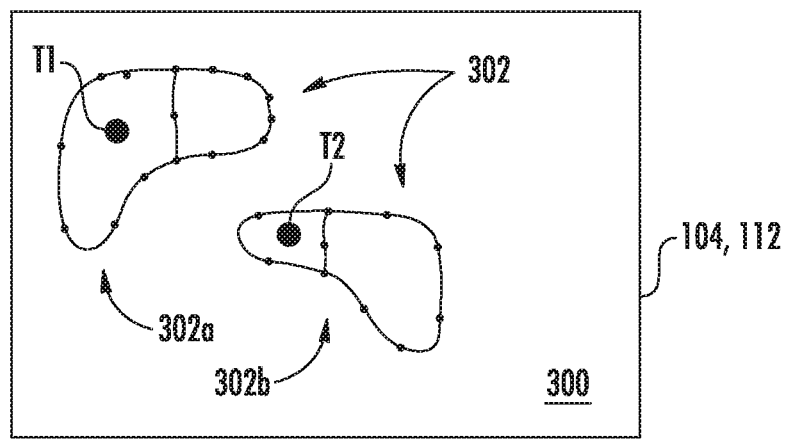
FIGS. 4A-4C are illustrations of the view of FIG. 3 amended over time.
Figure 4B:
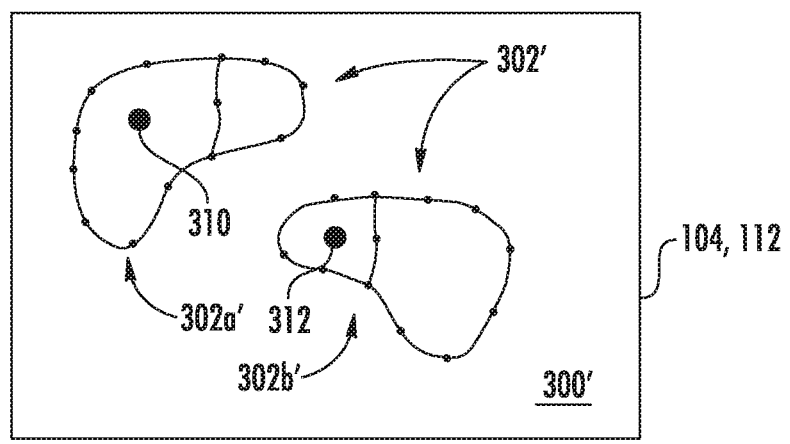
Figure 4C:
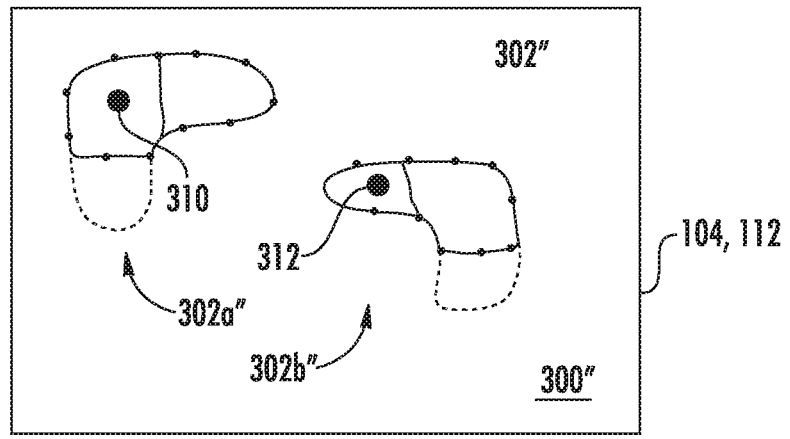

Referring now to FIGS. 4A-4C, previously described liver 302 is illustrated at varying points in time. During the course of treatment of patient "P", as the liver of patient "P" is surgically manipulated, either via ablation or resection, liver 302 is updated by clinicians to maintain an updated representation of the liver of patient "P", or liver 302. For example, during surgery a clinician may visually inspect the procedure performed on patient "P" by monitoring display 104 (FIG. 1) which projects images received from one or more imaging devices (not shown) in visual range of the liver of patient "P". As the clinician visually inspects the procedure being performed, the clinician may interact with workstation 102 to input areas along liver 302 which have received energy.

More particularly, the following sequence, provided for illustrative purposes only, illustrates modification of liver 302 stored in memory 202 over the course of three surgeries. As illustrated in FIG. 4A, during an exploratory surgery performed on patient "P" to determine the extent to which the liver of patient "P" is diseased, the clinician inspecting the procedure may note any anatomical landmarks or areas of interest. Such anatomical landmarks may include abnormal shaping of the liver of patient "P" or any features which visually indicate that tissue of the liver of patient "P" is diseased. Diseased portions of the liver of patient "P", identified as tumors "T1" and "T2", may be marked as described above on liver 302, as illustrated in FIG. 4A. To modify the default representation stored in memory 202, liver 302, the clinician selects one or more anchor points 306 with input device 210. The clinician may delete anchor points 306 or reposition anchor points 306 along liver 302. Repositioning anchor points 306 may cause associated splines 308 to be modified so as to more accurately represent the liver of patient "P". Similarly, clinicians may add anchor points 306 and splines 308 to approximate the position of tumors "T1", "T2" along liver 302. Tumors "T1", "T2" may further be associated with details such as, without limitation, the measured size of tumor "T1", "T2", the shape of tumor "T2", "T2", and the position of tumor "T1", "T2" relative to neighboring anatomical structures.

Referring now to FIG. 4B, during a second procedure performed by clinicians to ablate a portion of target tissue of the liver of patient "P", a first ablated region 310 and a second ablated region 312 may be recorded by clinicians, resulting in an updated representation of the liver of patient "P", the representation referred to as liver 302'. The first and second ablated regions 310, 312 recorded on liver 302' indicate regions of the liver of patient "P" which have received electrosurgical or cryo-energy (hereinafter "energy"). The clinician may approximate the general area along the liver of patient "P" when marking the first and second ablated regions 310, 312 based on visual inspection of the liver of patient "P". Additional information may be recorded by the clinician including the energy level (current level or, microwave frequency, etc.) of the energy applied to form the first and second ablated regions 310, 312, the duration which energy was applied to target tissue of patient "P", or other such information which is determined to be desirable in providing context for subsequent procedures. As illustrated in FIG. 4B, the ablated regions 310, 312 of liver 302' replace tumors "T1", "T2". Such replacement, by virtue of their existence in time relative to the entry of the ablated regions 310, 312 in the history of patient "P", may indicate to clinicians that the target tissue associated with tumors "T1", "T2" was ablated at the time which the ablation regions 310, 312 were recorded.

Additionally, or alternatively, the workstation 102 may receive sensor signals from imaging devices (not shown) used during the surgical procedure and convert the sensor signals to an image or series of images of the liver of patient "P". The workstation 102 may then superimpose the image or series of images onto the representation of the liver of patient "P", i.e., liver 302'. Once the clinician records the first and second ablated regions 310, 312 on liver 302 the image or series of images of the liver of patient "P" may be stored in memory 202.

Referring now to FIG. 4C, during a third surgical procedure performed by clinicians on the liver of patient "P", a portion of the liver of patient "P" is removed. In response to the removal of the portion of the liver of patient "P", the clinician visually inspecting the removal modifies the representation of the liver of patient "P". More particularly, the clinician may select and reposition one or more anchor points 306 which define the extents of the region of the liver of patient "P" which were removed. As the clinician repositions anchor points 306 included in view 302a" corresponding anchor points 306 on view 302b" are updated to reflect the revised position of anchor points 306. Similarly, if the clinician causes additional energy to be applied to the liver of patient "P", first and second ablated regions 310, 312 may be extended by repositioning anchor points 306 illustrated on interface 300" of workstation 102. Additionally, anchor points 306 may be added, along with corresponding splines 308 connecting the added anchor points 306, to form additional ablation regions along the liver 302 of the patient "P" (See FIG. 6). In a manner similar to those described hereinabove, subsequent ablation regions (not explicitly shown) may be recorded on liver 302" (see FIG. 6).

Figure 5:
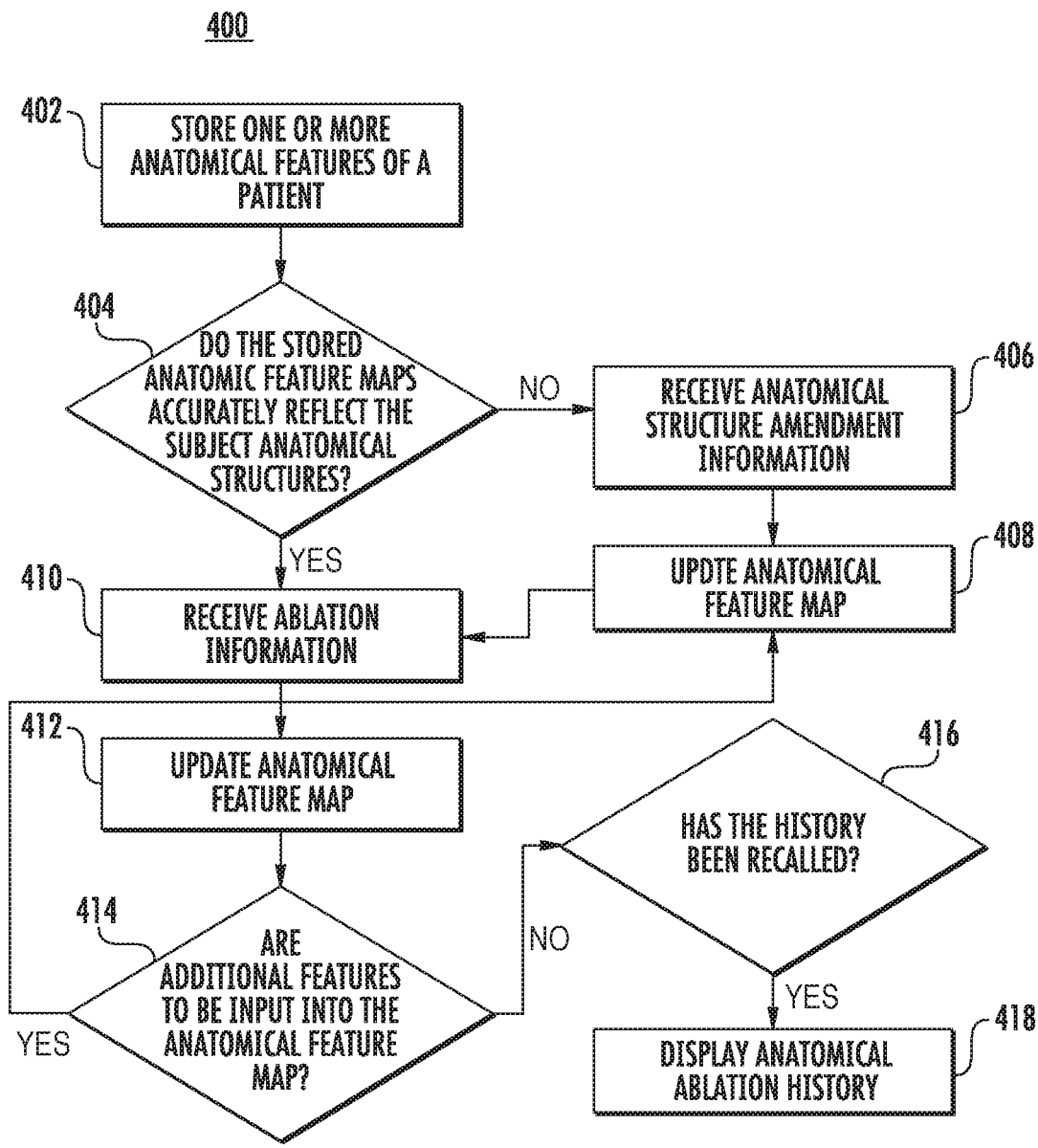
FIG. 5 is a flow diagram illustrating a method of recording ablation procedure data.

Referring now to FIG. 5, a flow diagram illustrating a process of recording an ablation history of patient "P" is illustrated, the process designated generally 400. While it is contemplated that a variety of anatomical structures, such as the liver, colon, kidneys, etc., of a patient may be acted upon or monitored by process 400, for purposes of clarity reference will be made to the initialization and updating of records of a liver of a patient "P".

A clinician initializes or instantiates a patient history associated with ablation procedures performed on a patient "P" (FIG. 1) (S402). During initialization, the clinician selects one or more default anatomical features stored in memory 202, the selected anatomical features associated with ablation procedures to be performed and recorded, such as liver 302 (FIG. 3) of patient "P". Once the anatomical feature, liver 302, is selected the clinician may further select views, such as the first and second views 302a, 302b (FIG. 3) of liver 302, to be maintained during process 400. The views 302a, 302b may be oriented by the clinician to show portions of liver 302 which include tissue to be ablated.

To correct for any deviations between the liver of patient "P" and the representation of the liver of patient "P" (liver 302), clinicians may modify liver 302 prior to ablation procedures to more accurately reflect the liver of patient "P". For example, if any landmarks of the liver of patient "P" deviate from landmarks represented on liver 302, such as deformations or growths which exist on or along the liver of patient "P", the clinician may add or relocate anchor points 306 (FIG. 3) to increase the accuracy of the representation of the liver of patient "P" (liver 302) (S408). To amend liver 302, the clinician may interact with the input devices 210 of workstation 102 or remote workstation 110 to reposition, add, or remove anchor points 306 associated with liver 302. During amendment of liver 302, anchor points may likewise be added or removed to indicate future areas of the liver of patient "P" to be targeted for ablation or new growths forming along the liver of patient "P".

During surgical procedures, images of the liver of patient "P" are transmitted to the display 104 of workstation 102 and are displayed during the surgical procedure (S410). By displaying liver 302 on the display 104 during the surgical procedure, clinicians may review information recorded prior to the procedure, such as areas intended for ablation during the present or subsequent ablation procedures. Images transmitted to display 104 may include procedure-specific information associated with the ablation of the liver of patient "P". As a result, clinicians may review notes taken before the procedure such as, without limitation, the amount of energy at a given power level for application during the procedure to the liver of patient "P" or an area or areas which were ablated during previous procedures.

Additionally, during the surgical procedure, clinicians may engage the workstation 102 to record procedure-specific information observed during the procedure. For example, an electrosurgical instrument or ablation device 118 (FIG. 1) used to perform the ablation procedure may be in electrical communication with workstation 102. As the clinician causes ablation device 118 to transmit energy to target tissue of the liver of patient "P", the ablation device 118 may transmit sensor data measured by one or more sensors (not explicitly shown) associated with ablation device 118, the sensor data indicative of the state of ablation device 118. More particularly, sensor data received from ablation device 118 may include information indicative of the power or current at which energy is being delivered to the target tissue, the duration of time associated with the delivery of energy, the model or configuration of ablation device 118, attachments coupled to ablation device 118, the temperature of ablation device 118 and the like. Ablation device 118 may transmit sensor signals indicative of one or more tissue properties such as tissue temperature, tissue thermal mass, tissue dielectric constant, tissue stiffness and tissue impedance. The sensor data received from ablation system 116, and more particularly ablation device 118, may be recorded in memory 202 for future recall and display on display 208.

As target tissue located along the liver of patient "P" receives energy during ablation procedures, clinicians monitoring the display 104 of workstation 102 (FIG. 1) may selectively record and associate information received by workstation 102 with liver 302 (FIG. 3) during ablation procedures (S412). Recordation may include adding anchor points 306 and splines 308 to reflect the extents of one or more newly formed, or extended, ablation regions 310, 312 (FIG. 4B) created during surgical procedures. Additionally, information may be recorded such as the time at which the ablation procedure occurred (e.g., a "time stamp"), the date on which the ablation procedure forming either of the ablation regions 310, 312 occurred, and other similar information.

Clinicians monitoring the display 104 of workstation 102 may also associate select ablation regions 310, 312 with sensor data received at the workstation 102 from the ablation device 118 during surgical procedures. For example, as energy is applied, the mode or manner in which the energy is transmitted to the target tissue (i.e., to cut, coagulate, fulgurate, etc.) may be recorded and associated with ablation regions 310, 312. Likewise, information indicative of the amount of energy applied to the target tissue (i.e., the current level of energy passing to the target tissue) may be recorded. When clinicians review the history of patient "P" to determine subsequent therapeutic treatments, the recorded information may be recalled and displayed on display 104, 112, thereby permitting the clinician to evaluate which ablation procedures were effective in treating the target tissue.

Once anatomical features such as liver 302 (FIG. 3) are updated by clinicians monitoring and engaging workstation 102 or remote workstation 110, data associated with liver 302 is transmitted to database 108. Transmitting data associated with liver 302 to database 108 permits electrical communication of the ablation data associated with liver 302 between workstation 102 and remote workstation 110. This persistent maintenance of information associated with liver 302, representing the liver of patient "P", enables clinicians to provided therapeutic treatments to patient "P" while simultaneously reviewing and updating the ablation history of patient "P".

If ablation is to be performed on multiple anatomical features, i.e., the liver and colon of patient "P", clinicians may identify the additional anatomical features to be monitored (S414). For example, if growths are identified on the liver of patient "P" as well as the colon of patient "P", the clinician engaging with either workstation 102 or remote workstation 110 and identify the views of identified anatomical structures desired. Once the additional anatomical feature is identified the clinician may modify the default representation of the additional anatomical feature (S408). Similar to the procedure associated with the liver of patient "P", representations of the corresponding anatomical structures may be updated by clinicians monitoring workstation 102 during surgical procedures (S412), and stored in database 108 for later recall and modification.

If, during the course of treating patient "P", clinicians determine that it would be desirable to review the ablation history of patient "P", clinicians may engage either workstation 102 or remote workstation 110 to retrieve the one or more representations of anatomical structures associated with patient "P" (S416). For example, during review of the history of patient "P" across the three ablation procedures illustrated in FIGS. 4A-4C, clinicians may recall any or all of the illustrations stored in memory 202 of liver 302 (i.e., liver 302, liver 302', or liver 302''') for review on workstation 102 or remote workstation 110 (S418). Upon recall, the ablation history of the patient "P" is displayed on the display 104 or the remote display 112 of the ablation recording system 100. It will be understood that recall and later display of the ablation history of the patient "P" may occur independent of process 400. If no recall is requested, process 400 terminates.

Figure 6:
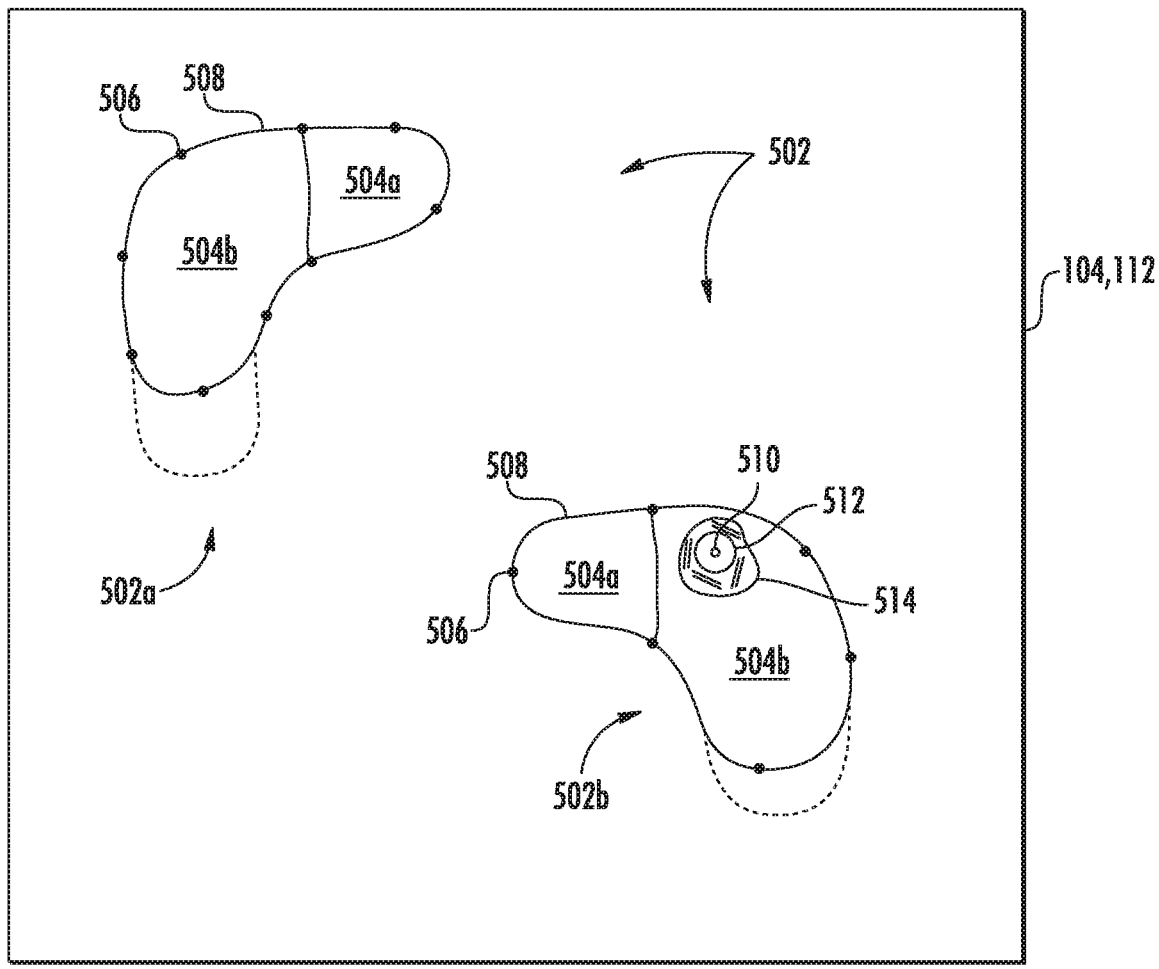
FIG. 6 is an illustration of a heat map including multiple ablation regions recorded on an anatomical feature, according to an embodiment of the present disclosure.

Clinicians, having all three representations of the liver of patient "P" to review, may subsequently determine which therapeutic treatments are desirable, as well as assess the progress of patient "P" across multiple therapeutic (ablative) treatments. Determinations may be made by visually inspecting each illustration of liver 302 stored in memory (see FIGS. 4A-4C). Alternatively, clinicians may recall liver 302 for display with the entire recorded ablation history represented thereon. For example, as illustrated in FIG. 6, a representation of the liver of patient "P", identified as liver 502, may display ablation regions 510, 512, 514 of target tissue juxtaposed on a first and second view 502a, 502b of liver 502. Specifically, as an ablation radius expands across a first, second, and third ablation procedure, liver 502 may be updated to show the position of each region relative to liver 502, a first ablation region 510, a second ablation region 512, and a third ablation region 514 being associated with the first, second, and third ablation procedures, respectively. The first, second, and third ablation procedures may occur during a single procedure, or during separate ablation procedures. The juxtaposition of each ablation region 510, 512, 514 an illustration of liver 502, referred to herein as heat map 500, permits clinicians to recall the ablation history of patient "P". Additionally, heat map 500 enables clinicians to associate data collected during the surgical procedures such as the power level and duration during which ablation was performed to create each ablation region 510, 512, 514. This association of data may subsequently enable clinicians to determine subsequent treatments for patient "P".

While description of the present disclosure is made with reference to certain example anatomical structures, it is to be understood that systems and methods described by the present disclosure are not intended to be limited to such anatomical structures. For example, it is contemplated that the systems and methods described herein may be used to record treatment and/or ablation information associated with vessel trees as well as pathways throughout the body of patient "P". Such pathways include, without limitation, biliary duct paths, bronchial paths, arterial paths, and the like.

Additionally, the information received at workstation 102 or remote workstation 110 may be referenced or recalled while traversing one or more channels of the body of patient "P". Specifically, channels, as well as vessel structures, may be identified as having one or more growths to be targeted during multiple ablation procedures. For example, a clinician may identify one or more bronchial tubes as part of an overall branched structure as having one or more abnormal growths. As the clinician traverses the bronchial tubes of patient "P" with ablation device 118, the clinician may refer to a representation of the bronchial tubes of patient "P" (not shown) on workstation 102 to determine where the growths exist and, subsequently, where target tissue is located to be ablated. As described above, representations of anatomical features may be viewed prior to surgical procedures to assist clinicians in determining where target tissue is located for treatment. For a detailed description of navigation through branched structures of a patient, reference may be made to commonly-owned U.S. Patent Publication No. 2016/0000302, the entire contents of which are incorporated herein by reference. Similarly, for a detailed description of percutaneous navigation through tissue of a patient, reference may be made to commonly-owned U.S. Patent Publication No. 2016/0317229, the entire contents of which are incorporated herein by reference.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system for storing and recalling ablation information, the system comprising:
   a workstation having a display, a user input device, and a memory, the workstation configured to be in electrical communication with an ablation device; and
   control circuitry in electrical communication with the ablation device and the memory, the control circuitry configured to:
   display a default anatomical structure on the display of the workstation;
   modify the displayed default anatomical structure to cause an appearance of the displayed default anatomical structure to reflect an appearance of a corresponding anatomical structure of a patient;
   receive input to add at least one anchor point to the displayed default anatomical structure to cause the appearance of the displayed default anatomical structure to depict a tumor corresponding to a tumor on the corresponding anatomical structure of the patient;
   position the depiction of the tumor on the displayed default anatomical structure to correspond to a position of the tumor on the corresponding anatomical structure of the patient;
   shape the depiction of the tumor on the displayed default anatomical structure to correspond to a shape of the tumor on the corresponding anatomical structure of the patient;
   further modify the displayed default anatomical structure to cause the appearance of the displayed default anatomical structure to reflect a region of the corresponding anatomical structure of the patient that was ablated via delivery of energy from the ablation device to the corresponding anatomical structure of the patient; and
   record, in the memory of the workstation, a level of the energy delivered from the ablation device to the corresponding anatomical structure of the patient and a duration of time that the energy was delivered from the ablation device to the corresponding anatomical structure of the patient.

2. The system of claim 1, wherein the default anatomical structure is stored in the memory of the workstation and configured to be selected by the control circuitry.

3. The system of claim 1, wherein the region of the corresponding anatomical structure of the patient that was ablated includes a first ablation region and a second ablation region at least partially intersecting the first ablation region.

4. The system of claim 3, wherein the control circuitry is configured to cause the display to display the default anatomical structure and at least one spline intersecting the displayed default anatomical structure to delineate the first ablation region from the second ablation region.

5. The system of claim 4, wherein the first ablation region is illustrated with a first color and the second ablation region is illustrated with a second color.

6. The system of claim 1, wherein the control circuitry is configured to receive input to remove a portion of the displayed default anatomical structure in response to a resection of a corresponding portion of the corresponding anatomical structure of the patient, thereby causing the appearance of the displayed default anatomical structure to reflect the resection of the corresponding portion of the corresponding anatomical structure of the patient.

7. The system of claim 1, wherein the control circuitry is configured to size the depiction of the tumor on the displayed default anatomical structure to correspond to a size of the tumor on the corresponding anatomical structure of the patient.

8. A system for storing and recalling ablation information, the system comprising:
    a workstation having a display device, a user input device, and a memory; and
    control circuitry in communication with the memory, the control circuitry configured to:
        display a default anatomical structure stored in the memory of the workstation on the display device;
        modify the displayed default anatomical structure based on input received via the user input device to cause an appearance of the displayed default anatomical structure to reflect an appearance of a corresponding anatomical structure of a patient;
        add at least one anchor point to the displayed default anatomical structure based on input received via the user input device to cause the appearance of the displayed default anatomical structure to depict a tumor corresponding to a tumor on the corresponding anatomical structure of the patient;
        position the depiction of the tumor on the displayed default anatomical structure to correspond to a position of the tumor on the corresponding anatomical structure of the patient;
        shape the depiction of the tumor on the displayed default anatomical structure to correspond to a shape of the tumor on the corresponding anatomical structure of the patient; and
        further modify the displayed default anatomical structure based on input received via the user input device to cause the appearance of the displayed default anatomical structure to reflect a region of the corresponding anatomical structure of the patient that was ablated via delivery of energy from an ablation device to the corresponding anatomical structure of the patient.

9. The system of claim 8, wherein the control circuitry is configured to record, in the memory of the workstation, a level of the energy delivered from the ablation device to the corresponding anatomical structure of the patient and a duration of time that the energy was delivered from the ablation device to the corresponding anatomical structure of the patient.

10. The system of claim 8, wherein the control circuitry is configured to remove a portion of the displayed default anatomical structure in response to a resection of a corresponding portion of the corresponding anatomical structure of the patient, thereby causing the appearance of the displayed default anatomical structure to reflect the resection of the corresponding portion of the corresponding anatomical structure of the patient.

11. The system of claim 8, wherein the control circuitry is configured to size the depiction of the tumor on the displayed default anatomical structure to correspond to a size of the tumor on the corresponding anatomical structure of the patient.

12. A system for storing and recalling ablation information, the system comprising:
    a workstation having a display device, a user input device, and a memory; and
    control circuitry in communication with the memory, the control circuitry configured to:
        modify a default anatomical structure stored in the memory of the workstation to cause an appearance of the default anatomical structure displayed on the display device to reflect an appearance of a corresponding anatomical structure of a patient;
        add at least one anchor point to the displayed default anatomical structure to cause the appearance of the displayed default anatomical structure to depict a tumor corresponding to a tumor on the corresponding anatomical structure of the patient;
        position the depiction of the tumor on the displayed default anatomical structure to correspond to a position of the tumor on the corresponding anatomical structure of the patient;
        shape the depiction of the tumor on the displayed default anatomical structure to correspond to a shape of the tumor on the corresponding anatomical structure of the patient;
        further modify the displayed default anatomical structure to cause the appearance of the displayed default anatomical structure to reflect a region of the corresponding anatomical structure of the patient that was ablated via delivery of energy from an ablation device to the corresponding anatomical structure of the patient; and
        record, in association with the region of the corresponding anatomical structure of the patient that was ablated, at least one parameter of the energy delivered from the ablation device to the corresponding anatomical structure of the patient.

13. The system of claim 12, wherein the control circuitry is configured to cause the display device of the workstation to display the region of the corresponding anatomical structure of the patient that was ablated juxtaposed on the displayed default anatomical structure.

14. The system of claim 12, wherein the control circuitry is configured to remove a portion of the displayed default anatomical structure in response to a resection of a corresponding portion of the corresponding anatomical structure of the patient, thereby causing the appearance of the displayed default anatomical structure to reflect the resection of the corresponding portion of the corresponding anatomical structure of the patient.

15. The system of claim 12, wherein the control circuitry is configured to size the depiction of the tumor on the displayed default anatomical structure to correspond to a size of the tumor on the corresponding anatomical structure of the patient.

* * * * *